United States Patent [19]
Band et al.

[11] Patent Number: 5,183,043
[45] Date of Patent: Feb. 2, 1993

[54] LOW RESISTANCE ELECTRICAL PICK-UP AND MANUFACTURE THEREOF

[75] Inventors: David M. Band, Surrey; David G. Penman, London, both of England

[73] Assignee: Surgicraft Limited, Redditch, United Kingdom

[21] Appl. No.: 613,904
[22] PCT Filed: Jun. 7, 1989
[86] PCT No.: PCT/GB89/00631
  § 371 Date: Jan. 28, 1991
  § 102(e) Date: Jan. 28, 1991
[87] PCT Pub. No.: WO89/11819
  PCT Pub. Date: Dec. 14, 1989

[30] Foreign Application Priority Data
  Jun. 8, 1988 [GB] United Kingdom ............... 8813570

[51] Int. Cl.$^5$ ............................................. A61B 5/402
[52] U.S. Cl. ..................... 128/642; 128/639; 29/825; 29/874
[58] Field of Search ............... 128/639, 642; 29/825, 29/874

[56] References Cited
U.S. PATENT DOCUMENTS

3,568,662 3/1971 Everett .................. 128/642 X
3,989,038 11/1976 Neward ................. 128/642
4,685,466 8/1987 Rau ........................ 128/642

OTHER PUBLICATIONS

Hon, "A Fetal Electrocardigraph Electrode", The Yale Journal of Biology and Medicine, vol. 39, No. 1, Aug. 1966, pp. 54–58.
Hon et al., "Electronic Evaluation of Fetal Heart Rate", Obstetrics and Gynecology, vol. 40, No. 3, Sep. 1972, pp. 362–365.
Hon, "Instrumentation ... Fetal Electrocardiography" Obsetrics and Gynecology, vol. 30, No. 2, Aug. 1967, pp. 281–286.

*Primary Examiner*—Lee S. Cohen
*Attorney, Agent, or Firm*—Trexler, Bushnell, Giangiorgi & Blackstone, Ltd.

[57] ABSTRACT

A low resistance electrical pick-up more particularly for use in a fetal scalp electrode or other bio-sensing electrode, is manufactured by applying to a length of stainless steel wire a first coating layer of nickel, and a subsequent coating layer of silver, an area of the silver layer then being chloridized and coated with bio-compatible plastics material, such as TECOFLEX ®. A layer of copper is preferably provided beween the nickel and silver layers, and it is also preferred for any further length or lengths of non-chloridized silver layer to be coated with a non-conducting varnish to avoid contact with body tissue.

14 Claims, 2 Drawing Sheets

LOW RESISTANCE ELECTRICAL PICK-UP AND MANUFACTURE THEREOF

BACKGROUND OF THE INVENTION

This invention relates to a low resistance electrical pickup—more particularly—but not exclusively—for use in a fetal scalp electrode or other biosensing electrode, and the manufacture thereof.

SUMMARY OF THE INVENTION

According to the present invention, a method of manufacture of a low resistance electrical pick-up is characterised by applying to a length of stainless steel wire a first coating layer of nickel, and a subsequent coating layer of silver, optionally with an intervening layer of copper, an area of the silver layer then being chloridized and coated with bio-compatible plastics material, e.g., TECOFLEX ®, a bio-compatible polyurethane resin. A further length or lengths of non-chloridized silver layer may be coated with a non-conducting varnish.

In a particular application of the invention to a fetal scalp electrode or other biosensing electrode of the type having an arcuate needle of stainless steel—which may serve as a reference electrode and/or measuring electrode and/or introducer for a separate electrode—the arcuate needle is plated with nickel and then silver, optionally with an intervening layer of copper, and an area of the silver layer at least on the outside of the curve of the needle, and possibly spaced from the point of the needle, is chloridized and then coated with bio-compatible plastics, and the remainder of the silver layer is coated with a non-conducting varnish.

The coating of the chloridized silver area can be given a thin coating of TECOFLEX by dipping it into a solution of TECOFLEX in tetrahydrofuran (THF) which is allowed to set (approximately 12 to 24 hours) before the remaining areas of the electrode are painted with a non-conducting varnish.

BRIEF DESCRIPTION OF THE DRAWINGS

A number of embodiments of the invention will now be described by way of example only, with reference to the accompanying diagrammatic drawings, in which.

Figure 1:
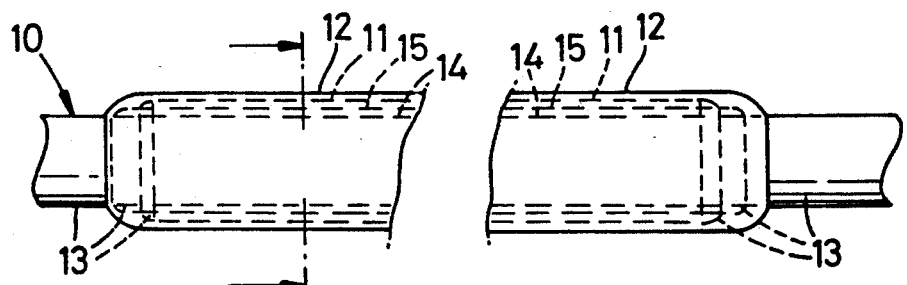
FIG. 1 is a fragmentary enlarged side elevation of a basic low resistance electrical pick-up manufactured in accordance with the invention.
Figure 2:
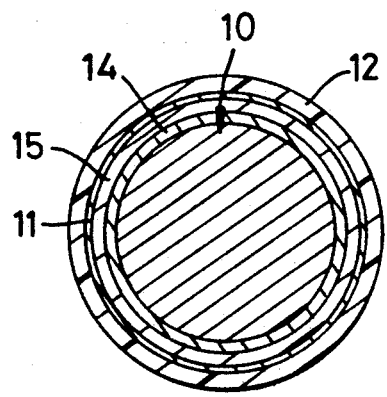
FIG. 2 is an even greater enlarged cross-section on the line II—II of FIG. 1.
Figure 3:
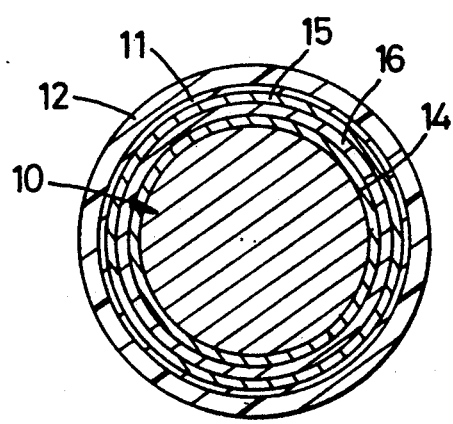
FIG. 3 corresponds to FIG. 2 but includes a slight modification.

The thickness of the coating layers in FIGS. 1 to 3 have been greatly exaggerated, even compared to the enlarged scale, for the sake of clarity.

DETAILED DESCRIPTION OF THE ILLUSTRATED EMBODIMENT

In FIGS. 1 and 2, a low resistance electrical pick-up comprises a length of stainless steel wire 10 having a first coating layer 14 of nickel, and a subsequent coating layer 15 of silver, an area (or length) 11 of the silver layer being chloridised (indicated in FIG. 1 by the thicker broken line) and then coated with bio-compatible plastics material 12, e.g., TECOFLEX. Further lengths 13 of non-chloridized silver layer 15, and preferably also adjacent exposed lengths of the nickel layer 14 and stainless steel wire 10 may be coated with a non-conducting varnish.

FIG. 3 corresponds closely to FIG. 2 but indicates a layer 16 of copper between the nickel layer 14 and the silver layer 15.

Figure 4:
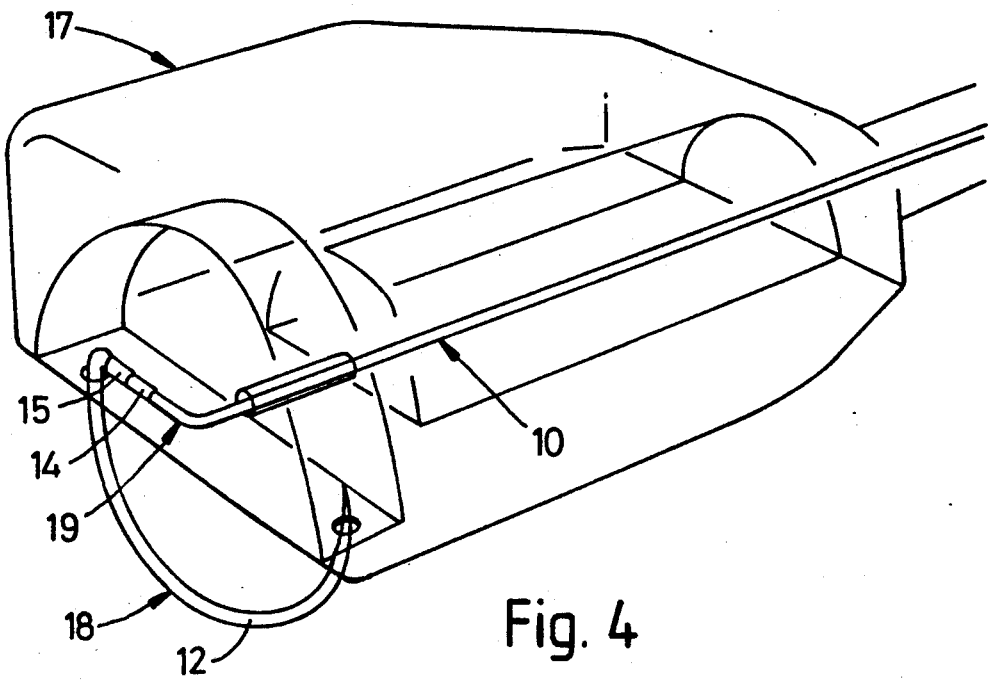
FIG. 4 is a greatly enlarged skeletal perspective view of the head member of a "Surgicraft-Copeland" fetal scalp electrode (FSE) including a low resistance electrical pick-up manufactured in accordance with the invention.

In FIG. 4, the head member 17 of a "Surgicraft-Copeland" FSE, as described in GB-PS 1 316 072 or GB-PS 1 523 263 (or U.S. Pat. No. 4,151,835), has an arcuate needle 18 formed on the outer end of a radial arm 19 from a main stainless steel wire 10, the arcuate needle 18 being plated with nickel 14 and then silver 15 (optionally with an intervening copper layer, not shown, but refer to FIG. 3), an area (not shown) of the silver layer at least on the outside of the curve of the needle 18, and possibly spaced from the point of the needle, is chloridized and then coated with bio-compatible plastics 12, and the remainder of the silver layer is coated with a non-conducting varnish.

Figure 5:
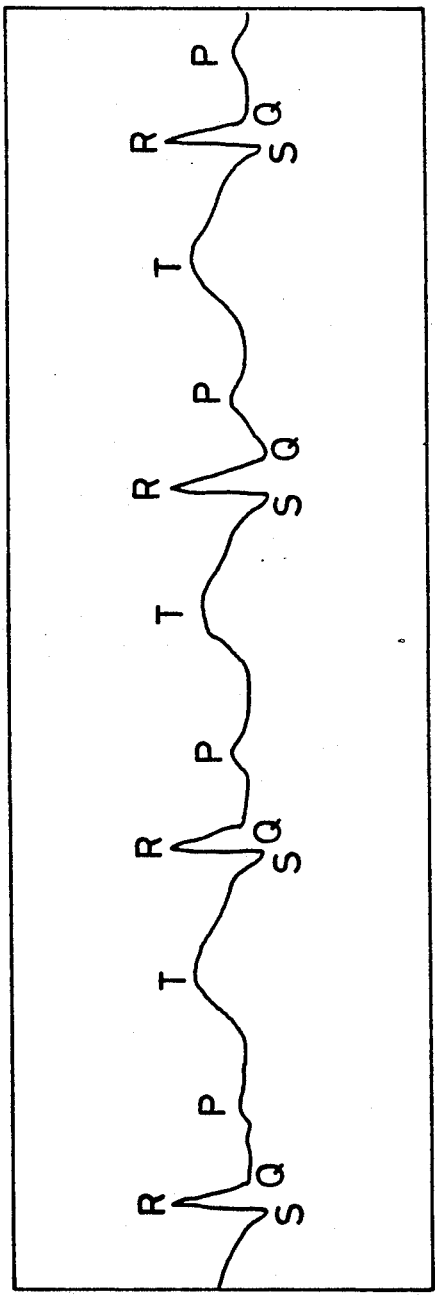
FIG. 5 is a fragmentary ECG trace obtained using a FSE as in FIG. 4.
Figure 6:
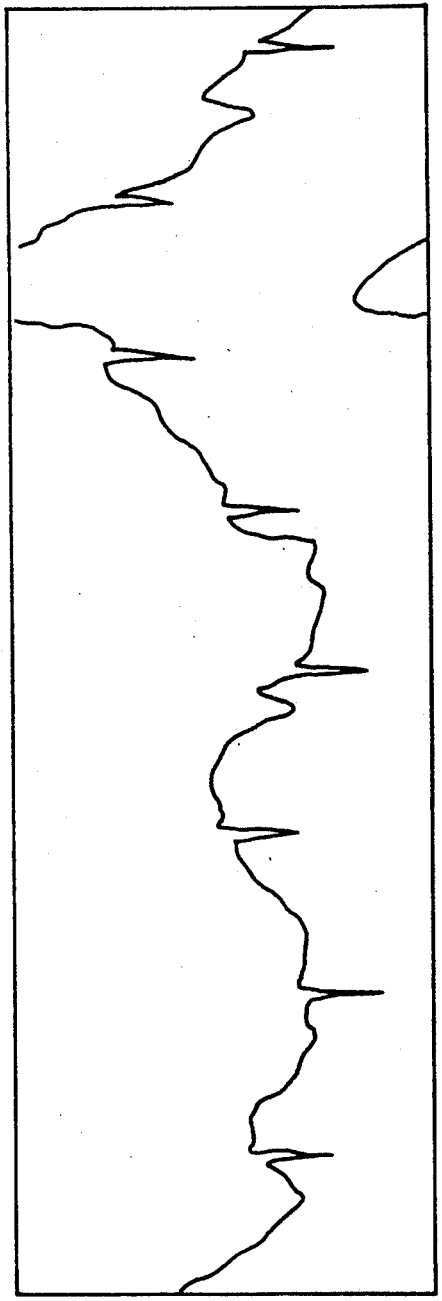
FIG. 6 is a fragmentary ECG trace obtained with an un-modified "Surgicraft-Copeland" FSE for comparison with the trace of FIG. 5, the paper speed in FIG. 5 being twice that in FIG. 6.

The fundamental advantage of the low resistance "Surgicraft-Copeland" FSE of FIG. 4 can be appreciated by comparing FIGS. 5 and 6. The bare stainless steel arcuate needle electrode of the unmodified "Surgicraft-Copeland" FSE is highly resistant to low frequency electrical activity, so the trace of FIG. 6 is erratic, and it also shows enormous variability because of the added effect of feto-maternal movement. In contrast, the trace of FIG. 5 shows that low frequency electrical activity from the fetus can be picked up with great accuracy by the low resistance "Surgicraft-Copeland" FSE of FIG. 4, and consistent waveforms (P,QRS and T waves) of the cardiac cycle can be more easily identified. This allows more complex fetal ECG waveform analysis and reduces the need for extensive signal processing and averaging, as has been necessary with the unmodified "Surgicraft-Copeland" FSE.

The invention is also applicable to other types of fetal scalp electrodes, such as the spiral electrodes of Corometrics Medical Systems Inc. U.S. Re. No. 28990, the clip-like electrodes of T.C. Neward EP 0 007 702, and the outwardly splayed electrodes of Kontron Inc. EP 0 099 077, or to other electrodes or probes, such as the outwardly splayed anchor needles in the cardiac probe of W. Mohl EP 0 004 967.

We claim:

1. A method of manufacture of a low resistance electrical pick-up characterised by applying to a length of stainless steel wire a first coating layer of nickel, and a subsequent coating layer of silver, an area of the silver layer then being chloridized and coated with bio-compatible plastics material.

2. A method as in claim 1, wherein the bio-compatible plastics material is TECOFLEX.

3. A method as in claim 1 or claim 2, wherein an intervening layer of copper is provided between the nickel and silver layers.

4. A method as in claim 1, wherein any further length or lengths of non-chloridized silver layer is/are coated with a non-conducting varnish.

5. A low resistance electrical pick-up manufactured by the method of claim 1.

6. A low resistance electrical pick-up as in claim 5, wherein the bio-compatible plastics material is TECOFLEX ®.

7. A low resistance electrical pick-up as in claim 5, characterised by an intervening layer of copper between the nickel and silver layers.

8. A low resistance electrical pick-up as in claim 5, characterised by a coating of a non-conducting varnish over any length of non-chloridized silver layer.

9. A method of manufacture of a fetal scalp electrode or other biosensing electrode of the type having an arcuate needle of stainless steel, characterised in that the arcuate needle is plated with nickel and then silver and an area of the silver layer, at least on the outside of the curve of the needle, is then chloridized and coated with bio-compatible plastics, and the remainder of the silver layer is coated with a non-conducting varnish.

10. A method as in claim 9, wherein the bio-compatible plastics is TECOFLEX.

11. A method as in claim 9 or claim 10, wherein an intervening layer of copper is provided between the nickel and silver layers.

12. A fetal scalp electrode or other biosensing electrode manufactured by the method of claim 9.

13. A fetal scalp electrode or other biosensing electrode as in claim 12, wherein the bio-compatible plastics is TECOFLEX ®.

14. A fetal scalp electrode or other biosensing electrode as in claim 12, characterised by an intervening layer of copper between the nickel and silver layers.

* * * * *